United States Patent [19]

Mandle et al.

[11] 4,265,855
[45] May 5, 1981

[54] SYSTEM FOR PERFORMING IMMUNOCHEMICAL AND OTHER ANALYSES INVOLVING PHASE SEPARATION

[75] Inventors: Richard M. Mandle, Pompton Lakes; Frank Karsai, Dover; Raymond S. Krautheim, Nutley, all of N.J.

[73] Assignee: Electro-Nucleonics, Inc., Essex, N.J.

[21] Appl. No.: 957,091

[22] Filed: Nov. 3, 1978
(Under 37 CFR 1.47)

[51] Int. Cl.³ .............................................. G01N 1/14
[52] U.S. Cl. .................................... 422/65; 73/425.6; 141/130; 422/63
[58] Field of Search .................. 422/65, 102, 71, 103, 422/101; 73/423 A, 425.6; 141/130

[56] References Cited

U.S. PATENT DOCUMENTS

| | | | |
|---|---|---|---|
| 3,533,744 | 10/1970 | Unger | 422/65 X |
| 3,762,879 | 10/1973 | Moran | 422/65 |
| 3,799,744 | 3/1974 | Jones | 422/65 |
| 3,883,305 | 5/1975 | Hoskins | 422/65 |

Primary Examiner—R. E. Serwin

[57] ABSTRACT

A system for automatically processing liquids in open-ended containers. The containers are moved past a plurality of operating stations that carry out the following operations: washing, reagent-adding, incubation, detection, and storage. The operating stations for washing and reagent-addition include vertically and horizontally movable assemblies for operating upon the containers. The containers are carried in groups in individual carrying blocks which are moved throughout the system.

16 Claims, 11 Drawing Figures

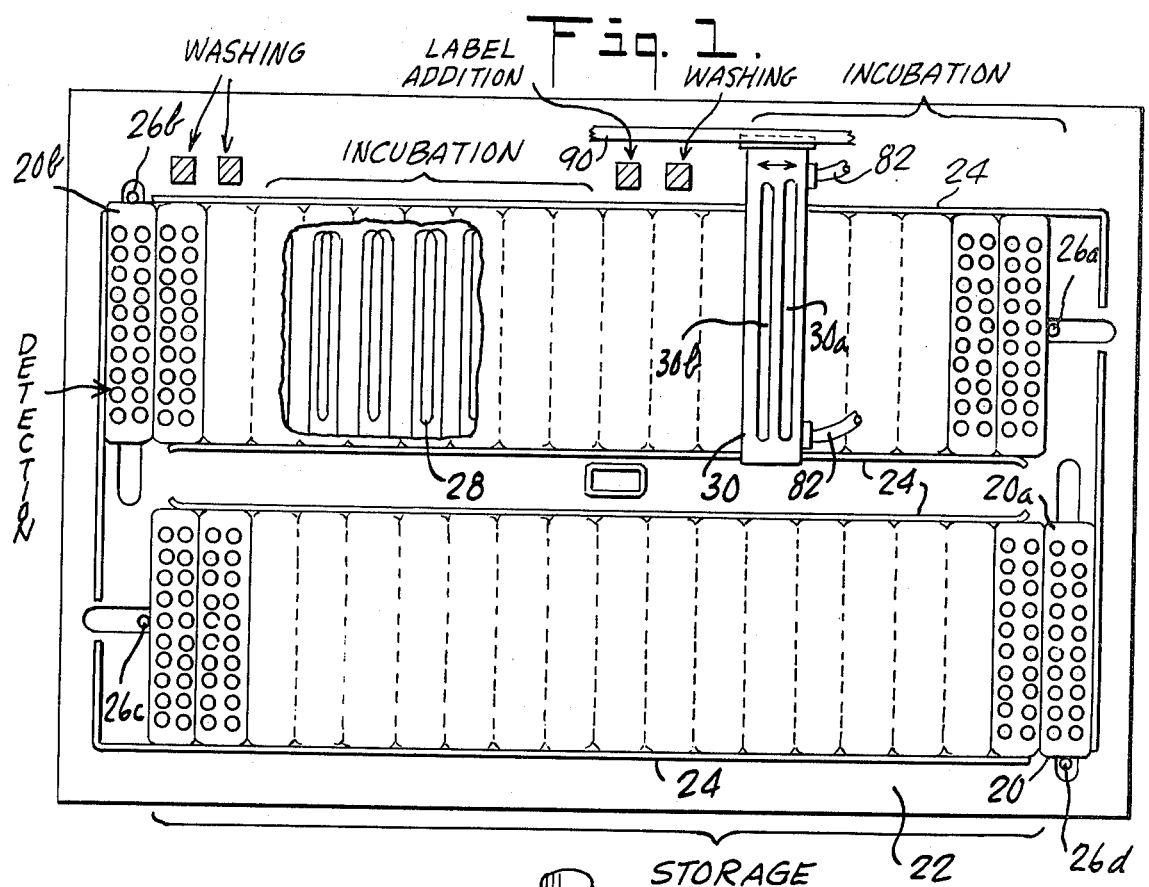
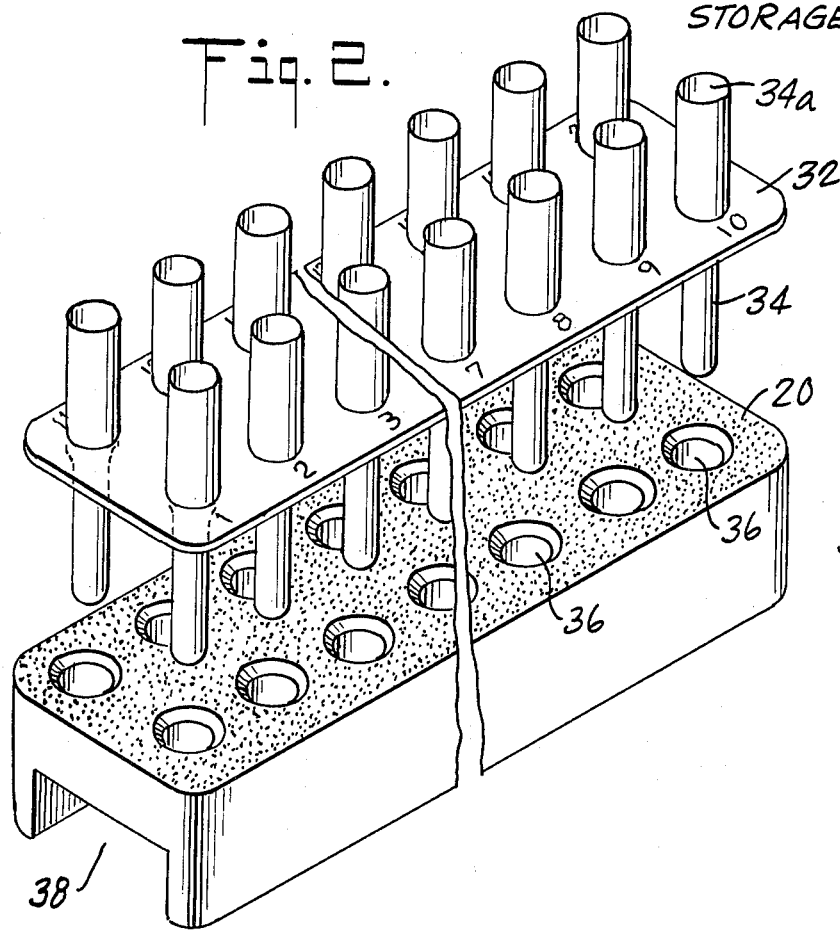
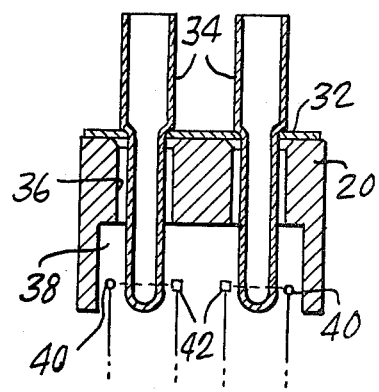

SYSTEM FOR PERFORMING IMMUNOCHEMICAL AND OTHER ANALYSES INVOLVING PHASE SEPARATION

BACKGROUND AND BRIEF DESCRIPTION OF THE INVENTION

This invention relates to the automatic processing of liquids in open-ended containers for testing purposes, and more particularly provides an automated system for detecting Hepatitis B. Surface antigen ($HB_sAG$) in human serum or plasma.

Many immunochemical reactions are performed by using what is known as a solid phase or phase separation system. Such analyses place one of the components on a solid support so it may readily be removed from the system during analysis. An example is the detection of $HB_sAG$, wherein the antibody to $HB_sAG$ is affixed to solid controlled pore glass particles (CPG). Such CPG is mixed in a test tube with a patient's serum. The serum in a diseased patient contains antigen to hepatitis, and under proper conditions the antigen may be made to react with the antibody on the CPG. A typical operation includes the removal of other serum proteins from those hepatitis associated proteins which adhere biologically to the CPG. This separation involves the use of aqueous washes, such as saline or phosphate buffers which allow the extraneous proteins to be removed without disturbing the chemical bond between the antigen and the hepatitis-associated proteins on the CPG. Identification markers or labels are also added in this analysis, but the excess quantity of these reagents usually must be removed also by washing or other phase separation techniques.

In performing a typical hepatitis assay, a patient's serum is incubated or mixed with CPG so that the required chemical reaction takes place. Next, buffer is added to and agitated with the patient's sample, and following agitation the CPG settles to the bottom of the test tube. Following settling, the liquid in the tube is aspirated or otherwise withdrawn, with the CPG remaining in the tube. Such buffer addition-agitation-removal may be repeated a number of times to remove most of the extraneous proteins. To verify the presence of an antigen adhering to the CPG, a label is added to the test tube which may be identified as, for example, by a coloring agent, an enzyme multiplication agent, or radioactive tag or a fluorescent agent incubation of the tagged label with the antibody antigen complex on the CPG forms a "sandwich". After a suitable incubation period, the excess label is removed by a wash in generally a number of washing steps. The material adhering to the CPG in the tube, as a sandwich, yields an indication which may be compared to known positive or negative controls to identify the patient's serum.

The operations outlined above are described in the brochure RIAUSURE®II published by Electro-Nucleonics Laboratories, Inc. These operations are tedious and require manual dexterity and continued operator attention to be properly carried out. The danger from operator fatigue and mistake, leading to false identification of a sample, is always present. In addition, variations in test parameters can occur from one test to another, leading to varying results.

It is desirable to optimize any immunochemical analysis by choosing proper conditions. While generally it is desirable to decrease the size of the CPG and the serum-carrying container (because the kinetics of the reactions will be faster and more reliable), the reduction of size creates problems in the manual handling of the tests, leading to errors.

The present invention provides for the automating of the $HB_sAG$ test procedure. It proceeds from the RIAUSURE® procedure of Electro-Nucleonics Laboratories, Inc. That procedure provides agitation and settling according to a programmed time schedule using small ferrite magnets placed inside each of the assay tubes. The test tubes are placed on an electro-magnetic assembly containing field coils energized by a digital counter, producing a varying field causing the magnets to move within the test tube and thereby agitate the serum-buffer-glass system within each tube. At an appropriate time, the magnetic field is deenergized, allowing the magnets to rest at the bottom of the test tubes, leaving a clear, supernatant liquid thereabove. A multiple head aspirater is employed to withdraw the supernatant liquid from the test tubes; a separate multiple head dispenser is used to introduce liquid along the wall of each test tube. The above cycle is completed manually and repeated until the tubes are properly washed. An appropriate label is added manually to each tube.

In the present invention, a card is utilized to hold a number of test tubes (e.g., twenty test tubes). The tubes are open-ended at the top thereof, and are carried by the card so that the bottom portions thereof extend below the card. The card rests on a carrying block, and the lower portions of the containers extend loosely into openings in the block. In this fashion, the test tubes are carried loosely by the block, facilitating later operations, as described below. A number of such blocks are positioned on a support table and are moved thereon in step-wise fashion around the table. Each tube contains a sample of a patient's serum along with magnetic particles, and underlying the table is a series of coils, the magnetic fields from which cause agitation of the magnetic particles and an appropriate mixing of the liquids within the test tubes. The test tube-containing blocks are caused to move in a rectangular pattern around the table in step-wise fashion by moving pins. The positions on the table provide for incubation, washing, label addition, detection, storage, and instrument cleansing. The washing assembly for adding a washing liquid to the test tubes and removing that liquid therefrom utilizes supply and aspirating heads positioned above the test tubes and movable vertically thereover. To process a number of test tubes simultaneously, the supply head includes a number of liquid supply tubes that communicate with a liquid supply manifold within the head. The aspirating head includes a plurality of aspirating tubes communicating with a vacuum chamber within the aspirating head. The aspirating and supply heads are movable vertically with respect to each other. Preferably, the supply tubes extend at an angle with respect to the vertical so as to wash the sides of the test tubes, and terminate within the supply head. The aspirating head is movable to move the aspirating tubes to positions in which they extend through and below the supply head and into the test tubes for aspirating liquid therefrom. To facilitate holding the test tubes, the supply head includes a test tube engaging portion in the lower part thereof for engaging the open ends of the test tubes. That lower portion of the supply head is movable vertically within the supply head and is yieldably biased to a lower position, moving upwardly upon engagement of the supply head with the test tubes. The supply head includes passages therein in which the supply tubes are positioned, and other passages for containing the aspirating tubes from the aspirating head thereabove. These passages terminate in a frusto-conical opening of increasing diameter to facilitate the positioning of the open-ended test tubes therein, facilitated by the loose holding of the test tubes in each carrying block.

Provision is made for washing the aspirating tubes to avoid carryover of contaminants.

Label addition is carried out by a label adding head preferably carrying two syringes, one for each of two rows of test tubes carried in a card. This head is moved vertically and horizontally to receive label and to dispense that label into the test tubes. The syringes are driven so that there is a slight drawing motion after each dispensing operation to prevent droplet leakage from the syringes.

Following passage of the test tubes through the system, the tubes are inspected, for example, by an appropriate radiometric or colorometric test.

The invention will be more completely understood by reference to the following detailed description which is to be read in conjunction with the attached drawings.

BRIEF DESCRIPTION OF THE DRAWINGS

FIG. 1 is a plan view of a presently preferred system embodying the invention.

FIG. 2 is a perspective view of a test tube carrying card and block assembly useful in practicing the invention.

FIG. 3 is a sectional view of the block of FIG. 2, with test tubes and card in position thereon, illustrating the inspection of two test tubes by appropriate light emitting and detecting cells.

DETAILED DESCRIPTION

Figure 4:
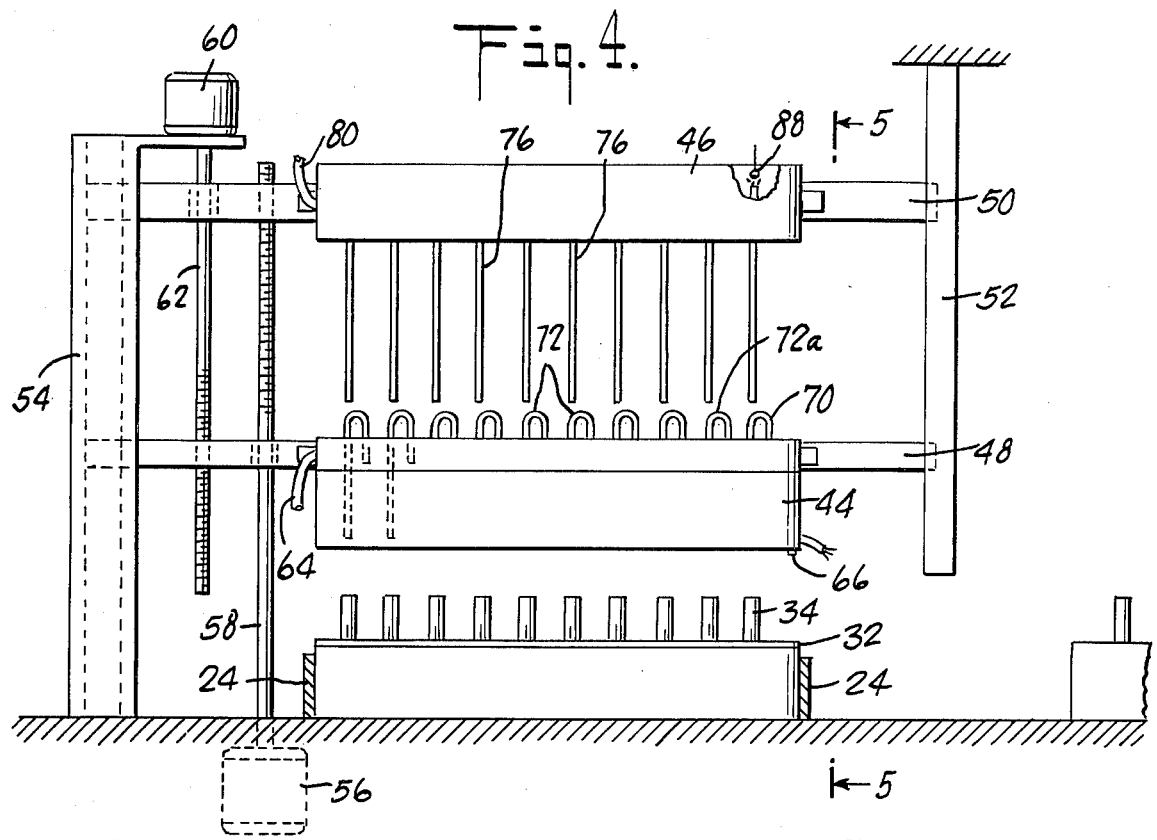
FIG. 4 is a side view of a washing station in the assembly of FIG. 1.

Referring to FIG. 1, a system for automatically carrying out the various steps of a $HB_sAG$ test is shown. A number of test tube carrying blocks 20 are positioned upon a support surface 22 for movement in step-wise fashion in a rectilinear pattern as guided by rails 24. Pusher pins 26a, 26b, 26c and 26d are employed, operated in appropriate sequence to move the blocks 20. The movement of the blocks is rectilinear, generally counterclockwise as viewed in FIG. 1. After each movement of the blocks, they all remain at rest for approximately 7.5 minutes and then are moved to the next position. Typically, the sequence of pin movement is the withdrawal of pins 26a and 26c (respectively moved to the right and to the left in FIG. 1), followed by the extension of pins 26b and 26d (respectively downwardly and upwardly as viewed in FIG. 1). In this fashion, the block designated 20a in the lower right-hand portion of FIG. 1 is moved from the forward row to the rear row, while the test tube carrying block designated 20b in the upper left-hand portion of FIG. 1 is moved from the rear row to the forward row. Following this movement of these two blocks at the ends of the respective rows, the pins 26a and 26c are extended respectively to move all the blocks 20 in the forward row at the lower portion of FIG. 1 to the right and all the blocks in the rear row in the upper portion of FIG. 1 to the left. The next movement of pins occurs approximately 7.5 minutes later, for example, allowing sufficient time for the various operations to be performed during the at rest positions of the test tube carrying blocks.

In FIG. 1, the various operations carried out in the system, to be described below, are indicated generally. It will be noted that the test tubes carried in the blocks generally undergo incubation during the eight positions of movement in the rear row of FIG. 1. It is assumed that each of the test tubes is filled with appropriate serum, in the case of the $HB_sAG$ test, and that appropriate negative and positive controls are included. As shown by the notations in FIG. 1, washing follows incubation, followed thereafter by label addition, followed thereafter by further incubation, followed thereafter by further washing, with a completion of these procedures at the time the block 20 reaches the position of the block 20b in FIG. 1. In this position of the block, appropriate detection of the test tubes may follow to characterize the serum under tests in each test tube. The front row of tube-carrying blocks is designated "storage"; no operations on the test tubes are carried out in these positions.

As noted above, the table includes coils 28 positioned thereunder which carry out the appropriate agitation of the contents of the test tubes, which include magnetic particles therein. Additionally, in FIG. 1, a wash tray 30 is included for washing aspirator needles used in the washing of the test tubes prior to label addition, as will be explained below.

Referring to FIG. 2, a typical test tube carrying block 20 is shown, along with a card 32 that carries test tubes 34. The card 32 carries two rows of ten test tubes each, but this number is simply representative. The card normally snuggly receives the test tubes 34, with their open ends 34a extending above the card and their closed, lower ends extending below the card and loosely into holes 36 in the block 20. As will be noted from FIG. 3, there is adequate space between the walls of the test tubes and the walls of the openings 36 in the block to permit movement of the card and test tubes. This movement facilitates in the registry of the test tubes with respect to the washing thereof, as will be explained in more detail below. As shown in FIG. 3, the block 20 is arch shaped in its lower portion, as at 38. This permits the entire block to pass over a detection station, which may include light emitting diodes 40 and photoelectric detectors 42, as shown in FIG. 3, which are mounted on the table of FIG. 1 in the detection station positioned under the block 20 in the position of the block 20b as shown in FIG. 1. Thus, a colorometric test may be utilized, e.g., for enzyme amplification, in which case the test tubes 34 would be of clear material. Other detection systems could be utilized, e.g., radiometric involving the counting of radioactivity as is typically used in the HB$_s$AG test procedure. In such case, the test tubes 34 could be opaque or clear.

Figure 5:
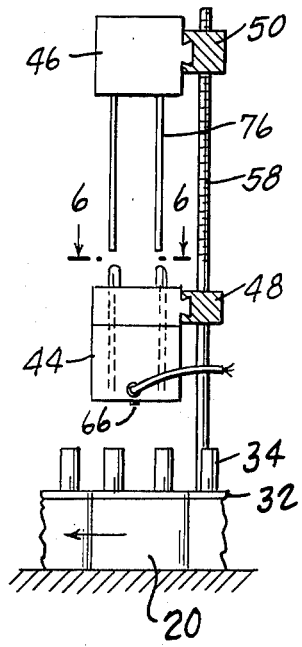
FIG. 5 is a sectional view taken along the section 5—5 in FIG. 4.

FIG. 4 shows a washing station, such as the washing station prior to the label addition station in the system of FIG. 1. That station includes a supply head 44 and an aspirating head 46 positioned above the test tubes 34 in a carrying block 20. The supply head 44 is for supplying a washing liquid to the test tubes, while the aspirating head 46 is for the purpose of aspirating from the test tubes the washing liquid. Referring to FIGS. 4 and 5 together, the heads 44 and 46 are carried in tongue and groove rail mountings 48 and 50, which permit the removal of these heads for cleansing, replacement, etc. The rails 48 and 50 are mounted for vertical movement in rails 52 and 54. A motor 56 drives the rail 50 up and down by virtue of a threaded drive shaft 58 which passes through the rail 48 and threadedly engages the rail 50. In similar fashion, a drive motor 60 drives the rail 48 upwardly and downwardly through use of a threaded drive shaft 62 which passes through the rail 50 and threadedly engages the rail 48. Appropriate timed vertical movement of the rails 48 and 50 is achieved through suitable control of the drive motors 56 and 60.

As noted above, prior to the washing operation, eight positions of incubation of the contents of the test tube take place, involving approximately one hour of incubation. During this time of incubation, the antigen to hepatitis contained in a diseased patient's serum contained in one of the test tubes reacts with the antibody of the CPG particles within the test tube. In the washing station, two separate washes with an appropriate buffer solution take place. The wash solution is supplied to the supply head 44 through an appropriate line 64. During the washing cycle, the motor 60 is energized to lower the supply head 44 downwardly. Before the washing solution is dispensed from the head 44, the detection of test tubes in position beneath the supply head is completed by a light generating and detecting unit 66 carried by the supply head 44. To this end, the cards 32 carrying the test tubes are typically colored white or light reflective, while the blocks 20 on their upper surface are colored black or light absorptive. If a card 32 is in place upon the block 20, light will be reflected sufficiently and detected by the unit 66, indicating the positioning of the test tubes in place to receive the wash solution. If a card 32 is not in position, indicating the absence of test tubes, then the light absorptive coating on the block 20 would absorb sufficient light so that no detection of light by the unit 66 would take place, indicating an absence of test tubes and ceasing further operation in the washing cycle, specifically preventing the supply of wash fluid from the supply head 44.

Figure 7:
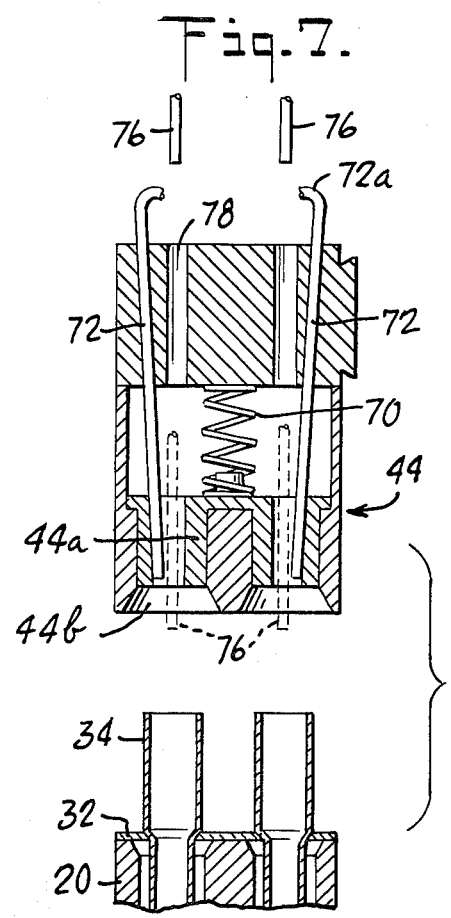
FIG. 7 is a sectional view (to an enlarged scale) of the assembly of FIG. 6, taken along the section 7—7.

The supply head 44 is shown in more detail in FIG. 7. It includes a lower test tube-engaging portion 44a which is slidable vertically and which is yieldably biased by a spring 70. The lower portion of the supply head 44 is frusto-conical, as at 44b, to facilitate in the positioning of the test tubes 34 properly in position with respect to the supply head. As that supply head is lowered, the test tubes bear against the head portion 44a, causing it to move upwardly against the biasing action of the spring 70.

Figure 6:
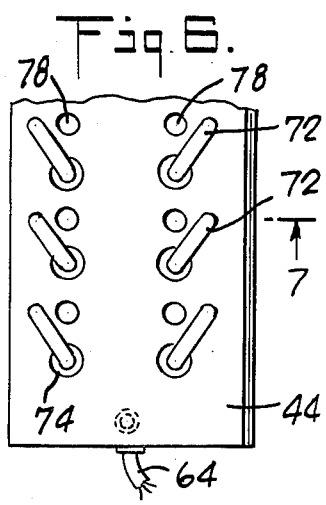
FIG. 6 is a sectional view (to an enlarged scale) of part of the assembly shown in FIG. 5, along section 6—6.

When the supply head 44 has engaged the test tubes 34, each test tube has positioned in the upper, open end thereof a liquid supply tube 72. That supply tube is angled with respect to the vertical (typically an angle of four degrees) so that the wash liquid impinges against the sides of the test tubes 34. The washing action is enhanced by such side impingement of liquid on the test tubes. The liquid supply tubes 72 loop upwardly and downwardly, as at 72a. It has been found that by so looping the liquid supply tubes, problems of dripping can be avoided. The supply tubes 72 are supplied with liquid from a chamber within the supply head 44 that is supplied with liquid from the liquid supply line 64. O-rings 74 may be used to provide an appropriate seal between the supply head 44 and the tubes 72 where the latter enter into the liquid supply chamber within the head 44 (FIG. 6).

During the washing operation, the aspirating head 46 is moved downwardly by appropriate energization of the motor 56 so that aspirating tubes 76 carried thereby extend downwardly through and below the supply head (through passages 78 in the supply head 44) to the positions shown in FIG. 7 in dashed lines. In these positions of the aspirating tubes 76, the tubes exhaust the liquid within the test tubes 34. The movement of the aspirating head 46 is such that the lower tips of the aspirating tubes 76 are just above the settled CPG in the test tubes 34. The aspirating of liquid takes place only after sufficient settling time has occurred so that the CPG and the magnets in the test tubes 34 have settled, preventing the aspiration of the CPG and magnets through the aspirating tubes. The aspirating tubes 76 communicate with a vacuum chamber within the aspirating head 46, which in turn communicates with an exhaust line 80 shown in FIG. 4.

In a typical HB$_s$AG test, 200 microliters of serum and 3 microliters by volume of CPG and 10 microliters by volume of magnets may be included in each of the test tubes 34. 1,000 microliters of washing solution may be used in each of two separate washes while the test tubes are in the washing station. Following the washing and aspiration of washing solution from the test tubes, the block 20 is moved to the next station in FIG. 1, which is for label addition. Prior to the next washing of a succeeding block 20, wash tray 30 shown in FIG. 1 is moved into position beneath the supply head 44 and aspirating head 46. The washing tray 30 contains two channels 30a and 30b which are supplied with liquid via supply and exhaust lines 82. Typically, liquid is pumped into the channels 30a and 30b in intermittent fashion so that a wave type movement of liquid within the channels occurs. The lower ends of the aspirating tubes 76 extend into these channels 30a and 30b and are completely washed thereby. During the washing of the aspirating tubes 76, vacuum is applied by the line 80 so as to aspirate liquid through the tubes 76 to ensure a complete cleaning thereof. This washing of the aspirating tubes removes all contamination, so that material from one test cannot contaminate another. Detection of the complete washing of the aspirating tubes 76 may be achieved by use of a probe 88 positioned in the aspirating head 46 within the vacuum chamber thereof opposite the end of each of the aspirating tubes 76. The spraying of cleansing fluid onto the probe 88 may complete an electrical circuit so that the passage of cleansing fluid is sensed. Failure to sense the flow of cleansing fluid can actuate a suitable alarm. The probe 88 may be used to sense the flow of washing liquid through the aspirating tubes during the washing of the test tubes as well as the washing of the aspirating tubes.

The wash tray 30 is movable horizontally back and forth by a drive motor (not shown) which moves the wash tray along a support rail 90.

Figure 8:
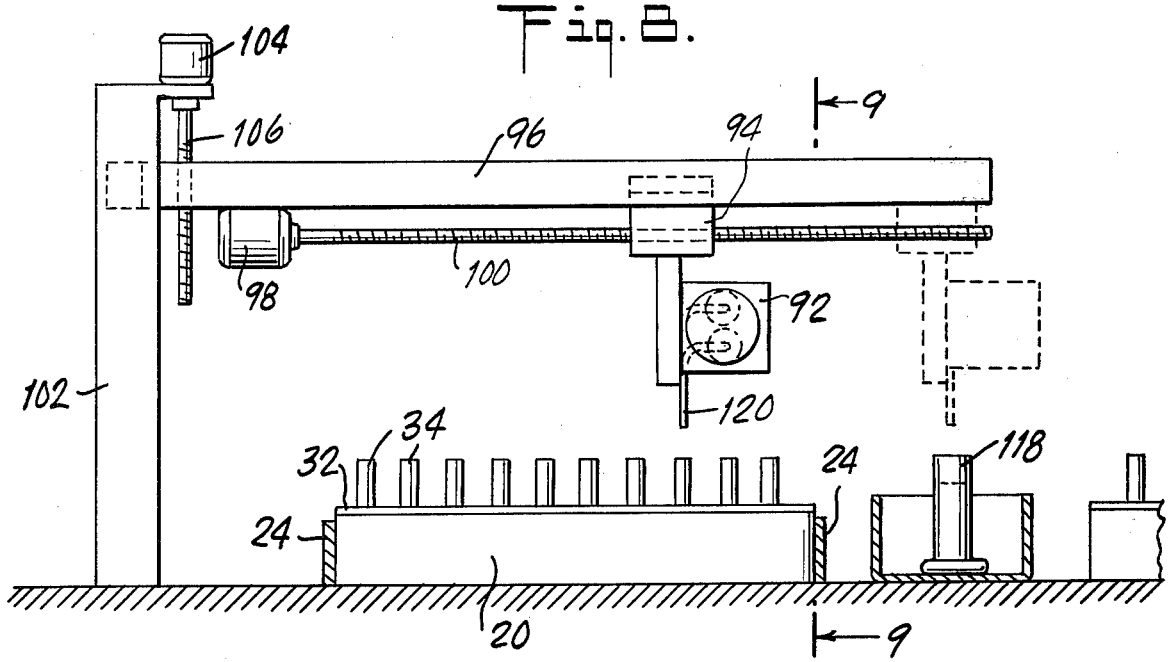
FIG. 8 is a side view of a label addition station in the system of FIG. 1.

FIG. 8 shows the details of the label addition station of FIG. 1. A label dispensing head 92 is carried by a mounting member 94 for horizontal movement along a rail 96. A motor 98 is mounted on the rail 96, and includes a threaded drive shaft 100 which threadedly engages the mounting member 94. Suitable energization of the motor 98 causes the mounting member 94 to move horizontally back and forth along the rail 96.

The label dispensing head 92 is also mounted for vertical movement through the mounting of the rail 96 on a vertical post 102 for vertical movement on that post. A motor 104 mounted on the post 102 drives a threaded drive shaft 106 which threadedly engages the rail 96. Suitable energization of the motor 104 moves the rail 96 vertically.

The label dispensing head 92 includes a pair of syringes 108 having piston members 110 therein. The piston members 110 are driven by a suitable drive motor 112 acting through drive shaft 114 that threadedly engages coupling 116 that joins together the two pistons.

Figure 9:
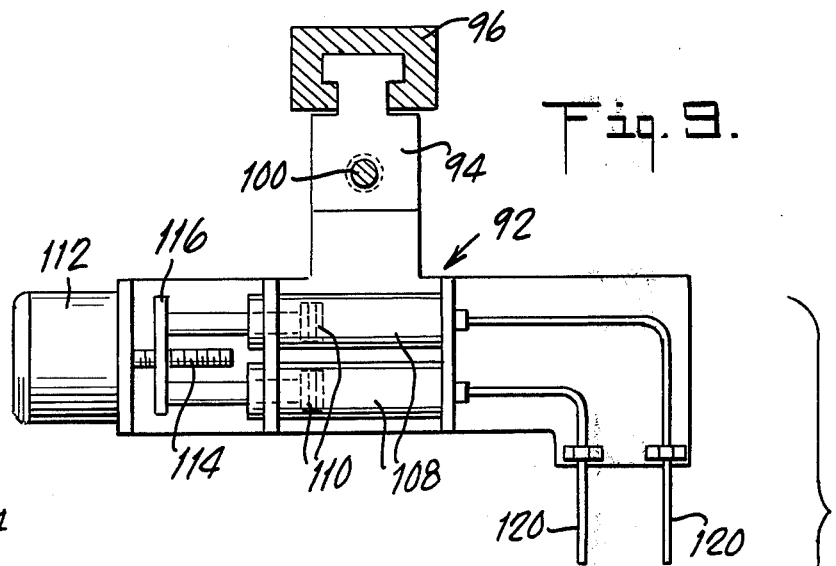
FIG. 9 is a sectional view (to an enlarged scale) taken along the section 9—9 in FIG. 8.

In operation, the motor 98 is first energized to move the label dispensing head 92 to the dashed line position shown at the right of FIG. 8. In this position, that label dispensing head is positioned over liquid label supply container 118. Next the drive motor 104 is energized, lowering the rail 96 and the dispensing head 92 so that syringe tubes 120 extend into the label supply container 118. Next the motor 112 is energized to move the pistons 110 to the left in FIG. 9, drawing label solution from the container 118 into the syringes 108 and thereby filling the syringes. Next the motor 104 is energized to raise the rail 96 and to remove the syringe tubes 120 from the supply solution. To avoid dripping, the motor 112 may be energized to drive the syringe pistons 110 slightly to the right (the dispensing direction) in FIG. 9 and then slightly to the left (the drawing direction in FIG. 9) to suck in liquid droplets at the end of the syringe tubes 120 to prevent droplet leakage from the ends of the syringe tubes. Next the motor 98 is energized to move the label dispensing head 92 in position above the first two test tubes 34 on the block 20 (the right most test tubes in FIG. 8). The motor 104 is next energized to lower the rail 96 so that the syringe tubes 120 are positioned appropriately within the test tubes 34. The motor 112 is then driven so that the syringe pistons 110 move to the right a measured distance to dispense a measured amount of label solution (typically 100 microliters). Following the dispensing operation, the motor 112 is energized to draw the syringe pistons 110 slightly to the left so as to suck in any droplets at the ends of the syringe tubes 120 and to prevent droplet leakage from those tubes. The motor 104 is energized to raise the head 92, the motor 98 is then energized to move the label dispensing head 92 to the next pair of test tubes 34, and the operation just described repeats.

Figure 10:
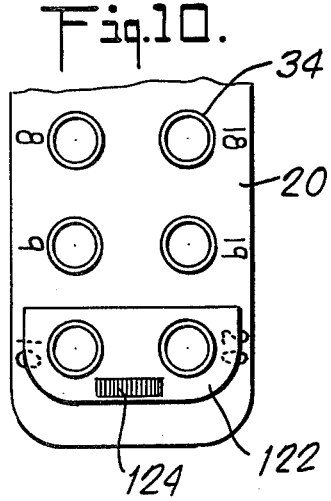
FIG. 10 is a plan view of a portion of one of the test tube carrying cards, showing an identifying magnetic card thereon.
Figure 11:
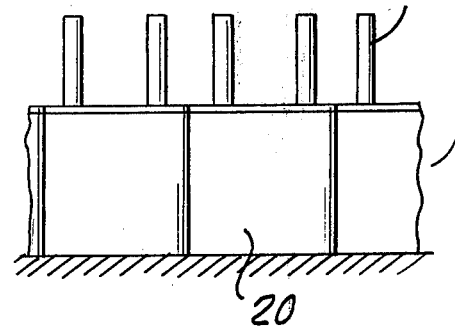
FIG. 11 is a perspective view of the magnetic card shown in FIG. 10.

Following the addition of label solution to all the test tubes, the block 20 moves through the incubation positions shown in FIG. 1. Following incubation, during which the labelled antibody added to each test tube undergoes reaction with the contents of the tube, the contents of each tube are again washed with a buffer solution as in the washing that took place following the first incubation as described above. The washing apparatus may be the same as that described above in connection with the washing following first incubation. Cleansing of the aspirating tubes through use of a wash tray may or may not take place, as desired. Typically, in the $HB_sAG$ test, elaborate cleaning of the aspirating tubes is not necessary, because contamination is not present within the test tubes as it is during the first washing operation described above. Following the final washing, which takes place at two washing stations, the CPG within the test tubes is ready for examination to determine the results of the test. Detection may take place when the test tube carrying block 20 is in the position of the blok 20b shown in FIG. 1, as described above. With reference to FIG. 10, the block 20 may include a tag 122 thereon which is magnetized, e.g., as at 124 as shown in FIGS. 10 and 11, for suitable detection of the test tube carrying block as it passes through the various stations within the system.

A presently preferred embodiment of the invention has been described above. Obviously, modifications could be made. Electrical coils beneath the test tube support table have been shown, in conjunction with magnetic particles within the test tubes. The coils could be replaced with an oscillating magnetic mat, if desired. Cooling coils could also be added, as well as thermastatically controlled heating elements. Controls for the detection of low level of reagents, washing solutions, and overfilling of various reservoirs can be utilized, as desired. Beginning of test and end of test detections may be used, as well as optical/electrical devices at the various liquid dispensing stations to sense liquid levels, liquid presence, and the like.

Further, while the device has been described in connection with a hepatitis test, any immunological test may be performed involving some or all of the various operations described above.

Accordingly, the invention should be taken to be defined by the following claims.

We claim:

1. A system for automatically processing liquids in open-ended containers comprising conveyor means for conveying said containers past a plurality of operating stations, one of said operating stations comprising a station for adding and removing a liquid respectively to and from said containers, said station comprising a head assembly engageable with at least one of said containers and including at least one liquid supply tube and at least one aspirating tube, said head assembly including means for positioning only one of said tubes within the open end of one of said containers at any time.

2. A system according to claim 1, in which said head assembly comprises a liquid supply head for supplying liquid to said liquid supply tube and an aspirating head for applying a vacuum to said aspirating tube.

3. A system according to claim 1, in which another of said operating stations comprises a reagent adding station for adding a reagent to said containers, said reagent adding station comprising a reagent dispensing head mounted for vertical and horizontal movement, for moving said reagent adding head to a first position in which reagent is supplied to said reagent adding head and thereafter to at least one dispensing position in which said reagent adding head is moved vertically successively to add reagent to a plurality of said containers, a washing tray, and means for moving said tray into a washing position beneath said supply and aspirating heads for washing said aspirating tube.

4. A system according to claim 2, in which said aspirating head is positioned over said supply head, and including means for causing relative vertical movement between said supply and aspirating heads to cause said aspirating tube to pass through said supply head.

5. A system according to claim 4, in which said supply head includes a container-engaging portion in the lower part thereof for engaging the open ends of said containers.

6. A system according to claim 5, in which said container-engaging portion is movable vertically within said supply head and is yieldably biased to a lower position, said container-engaging portion being movable upwardly upon engagement of said supply head with said containers.

7. A system according to claim 6, in which said container-engaging portion includes at least one passage therein in which said supply tube is positioned, said passage terminating in a frusto-conical opening of increasing diameter to facilitate the positioning of the open-ended containers therein.

8. A system according to claim 7, in which said containers are carried loosely in a carrying block to facilitate entry into said frusto-conical opening.

9. A system according to claim 8, in which said containers are carried by a card, the lower portions of said containers extending below said card, said card being carried on said block with said lower portions of said containers extending loosely into openings in said block.

10. A system according to claim 9, in which said card is light reflecting, and a least one of said heads includes light generating and detecting means positioned so as to be adjacent a card when said head is operative and, by the detection of reflected light from said card, generates a signal indicating the presence of said card with containers thereon in operative position with respect to said last-mentioned head.

11. A system according to claim 1, in which said supply tube is positioned at an angle with respect to the vertical to direct said liquid against the sides of said containers.

12. A system according to claim 1, including a reagent adding head which comprises at least one syringe having a piston member therein which is movable in a drawing direction to draw liquid into the syringe and in a dispensing direction to dispense liquid from the syringe, and including drive means for driving said piston in said drawing and dispensing directions, and control means controlling said drive means so as to cause said piston member to be driven slightly in the drawing direction following each movement of the piston in the dispensing direction to prevent droplet leakage from said syringe.

13. A system according to claim 1, including inspection means for inspecting said containers after they have moved past said operating stations.

14. In a system for automatically processing liquids in open-ended containers, a washing assembly for adding and removing a washing liquid respectively to and from said containers, said washing assembly comprising supply and aspirating heads positioned above said containers and movable vertically thereover, said supply head including at least one liquid supply tube communicating with a liquid supply manifold within said head, said aspirating head including at least one aspirating tube communicating with a vacuum chamber within said aspirating head, said aspirating and supply heads being movable vertically with respect to each other, said supply tube extending at an angle with respect to the vertical and terminating within said supply head, and said aspirating head being movable to move said aspirating tube to a position in which it extends through and below said supply head.

15. A system according to claim 14, in which said supply head includes a container-engaging portion in the lower part thereof for engaging the open ends of said containers, said container-engaging portion being movable vertically within said supply head and yieldably biased to a lower position within said head, said container-engaging portion being movable upwardly upon engagement of said supply head with said containers.

16. A system according to claim 15, in which said supply tube terminates at its lower portion within the container-engaging portion of said supply head, said container-engaging portion being movable with respect to said supply tube so that, when said container-engaging portion is moved upwardly upon engagement of said supply head with said containers, said lower end of said supply tube extends below said container-engaging portion.

* * * * *